(12) United States Patent
Brinz

(10) Patent No.: US 6,921,196 B2
(45) Date of Patent: Jul. 26, 2005

(54) DEVICE AND METHOD FOR TESTING A MATERIAL

(75) Inventor: Thomas Brinz, Bissingen Unter der Teck (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/124,841

(22) Filed: Apr. 18, 2002

(65) Prior Publication Data

US 2002/0176477 A1 Nov. 28, 2002

(30) Foreign Application Priority Data

Apr. 18, 2001 (DE) .......................... 101 18 782

(51) Int. Cl.[7] .................. G01N 25/00; G01N 31/10; G01J 5/00; G01K 13/00; G01K 7/00

(52) U.S. Cl. .................. 374/45; 374/121; 374/179; 374/141; 436/37; 436/159; 356/437

(58) Field of Search .................. 374/179, 145, 374/54, 5, 141, 120, 45; 436/37, 147, 159, 171; 422/83, 95; 356/437; 250/343, 346

(56) References Cited

U.S. PATENT DOCUMENTS

| | | | | |
|---|---|---|---|---|
| 3,488,155 A | * | 1/1970 | Ayers | .......................... 436/147 |
| 3,659,452 A | * | 5/1972 | Atwood et al. | ............. 73/31.03 |
| 4,042,333 A | * | 8/1977 | Dell et al. | .................... 73/23.2 |
| 4,170,455 A | * | 10/1979 | Henrie | .......................... 422/95 |
| 4,210,808 A | | 7/1980 | Miyatake | |
| 4,373,137 A | | 2/1983 | Fabinski et al. | |
| 4,397,556 A | * | 8/1983 | Müller | ........................ 356/301 |
| 4,764,023 A | * | 8/1988 | White et al. | ................... 374/29 |
| 5,468,962 A | | 11/1995 | Ohishi et al. | |
| 5,486,336 A | * | 1/1996 | Dalla Betta et al. | .......... 422/95 |
| 6,063,633 A | * | 5/2000 | Willson, III | .................. 436/37 |
| 6,494,080 B2 | * | 12/2002 | Fabinski et al. | ............ 73/31.05 |

FOREIGN PATENT DOCUMENTS

| | | |
|---|---|---|
| WO | 97 32208 | 9/1997 |
| WO | 98 07026 | 2/1998 |

OTHER PUBLICATIONS

Naumann et al., "A new electrical mine gas recorder," Glückauf, 94 (1958), Heft 37/38, pp. 1355–1361.*

* cited by examiner

Primary Examiner—Gail Verbitsky
Assistant Examiner—Mirellys Jagan
(74) Attorney, Agent, or Firm—Kenyon & Kenyon

(57) ABSTRACT

A device and a method for testing a material, particularly a catalytically active material, are provided. In accordance with the present invention, a substance mixture is chemically converted and a radiation unit, which allows the rapid characterization of the material without a great effort, is provided for generating radiation to be at least partially absorbed by the substance mixture. At least one temperature measuring device for measuring a temperature change caused by the absorption is also provided.

15 Claims, 1 Drawing Sheet

DEVICE AND METHOD FOR TESTING A MATERIAL

FIELD OF THE INVENTION

The present invention relates to a device and a method for testing a material.

BACKGROUND INFORMATION

Various methods may have been used for the development of materials and/or catalysts. Appropriate catalysts may be intended, for example, to change the gas composition of a gas. For this purpose, an appropriate gas may be guided past the catalyst. To test whether the catalyst converts the gas mixture, among other things, the heating of the catalyst caused by the conversion may be measured using an infrared-thermographic metering unit. In this case, for example, numerous catalyst samples of a great variety of types positioned side by side may be tested simultaneously.

Using this technique, it may be only determined whether a catalyst sample interacts with the gas mixture, i.e., whether it converts the gas mixture or not. However, it may not be determined in this manner whether the catalyst sample produces the desired product or whether an undesired product is produced instead.

Alternatively, gas chromatography methods may also be used in appropriate tests to determine the composition of the gas mixture conducted past the catalyst sample. Using these methods, in contrast to the method previously described, it may be determined whether the catalyst sample produces the desired product.

However, in this case, even one catalyst sample may require a considerable effort. Because of this, use in combinatorial chemistry, for example, in which as many different samples as possible are to be tested, may be limited.

SUMMARY OF THE INVENTION

In contrast, the present invention provides a device and a method for testing a material, particularly a catalytically active material, which may be designed for the chemical conversion of a substance mixture, for example a gas, a liquid, or the like, which may allow rapid characterization of the material without a substantial effort.

A device according to the present invention may be distinguished in that at least one temperature measuring device is provided for measuring a temperature change caused by absorption.

The temperature change and therefore, the desired conversion of the substance mixture, may be measured relatively rapidly both directly and indirectly with a relatively small effort with the aid of the temperature measuring device according to the present invention. The temperature measuring device may, for example, be configured as a radiation analysis device, particularly for direct measurement.

In general, the radiation spectrum of the radiation unit may be selected as a function of the absorption spectra of the desired substance or gas. For example, all radiation which are capable of causing a temperature change of certain materials, particularly microwave or infrared radiation, may be used in a device according to the present invention. In this case, the radiation may include a relatively narrow frequency band. A comparatively broad frequency band may also be scanned using a scanning unit.

The temperature measuring device may be configured as a thermocouple. With the aid of a thermocouple according to the present invention, the temperature change may be determined and analyzed accordingly with a small effort.

In an exemplary embodiment of the present invention, at least one chamber filled with a reference substance, particularly with a reference gas, may be provided. The reference substance or reference gas may correspond to a substance or gas and/or the substance mixture to be produced from the material. In this manner, according to the present invention, indirect testing of the material may be implemented.

In addition, a favorable ratio of the chamber volume to the incident radiant energy and shaping of the chamber volume may be configured for optimizing the temperature change according to the present invention.

The chamber may include a wall section which is at least partially transparent to the radiation. Using the corresponding wall section, the radiation of the radiation unit may penetrate into the chamber and may be absorbed by the reference substance or reference gas. If required, the wall section(s) may be configured in such a manner that the radiation may penetrate into the chamber and also vacate it.

The possibly converted substance mixture may be positioned between the chamber and the radiation unit. This measure may ensure that the radiation to be absorbed may penetrate the possibly converted substance mixture and may reach the chamber.

If, for example, the substance to be produced is not produced by the material to be tested, then a corresponding part of the radiation may not be absorbed, whereby the radiation is at least partially absorbed by the reference substance and may thus heat the reference substance and/or the chamber, which may be detected by the temperature measuring device according to the present invention and communicated to the analyzing unit.

In contrast, if the substance to be produced, i.e., the desired substance, is produced using the material to be tested, then the radiation may be at least partially absorbed by this substance, so that the reference substance of the chamber, which in particular may correspond to the desired substance, is not heated or cooled. This may be communicated to and analyzed by an appropriate analyzing unit using the temperature measuring device.

The corresponding description may also apply in the case in which the reference substance is the same as the substance mixture. In contrast to the previous example, the reference substance and/or the chamber may be heated if the substance mixture conducted past the material is converted. The reference substance and/or the chamber may be cooled or not heated if the substance mixture is not converted.

The corresponding temperature change caused by the absorption may in turn be measured using the temperature measuring device according to the present invention. The chamber may enclose the temperature measuring device for this purpose, which may result in a relatively rapid and/or sensitive measurement of the temperature change.

In an exemplary embodiment of the present invention, the chamber has a temperature regulation unit for regulating the chamber temperature. With the aid of an appropriate temperature regulation unit, the chamber may be regulated in such a manner that interfering, particularly external, temperature changes may be compensated, which may be used for significantly more precise determination of the temperature change and therefore testing of the material. The temperature regulation unit may be designed as a thermostat unit.

The material may be positioned essentially inside a tubular element or a hollow body element. Such elements may allow, expedient steering of the substance mixture or the gas.

In an exemplary embodiment of the present invention, a supply unit for supplying the substance mixture is positioned at one end of the tubular element. If a tubular element is used, the substance mixture may be supplied easily to the material to be tested using the appropriate supply unit.

The material may have the form of a powder. A powdered material may have a large surface which may be active catalytically, which may significantly improve the chemical conversion of the substance mixture or the gas mixture. Hereby, comparatively small sample quantities may be used for material testing, whereby the effort may be additionally reduced.

In addition, a powdered material may be adapted to any desired shape, among others, that of the tubular element. Furthermore, the material may be arranged over the entire cross-section of the tubular element. The powdered material may be arranged between two support elements permeable to the substance mixture.

In an exemplary embodiment of the present invention, the radiation unit may be positioned in such a manner that the radiation penetrates the tubular element behind the material in the flow direction of the substance mixture, whereby the converted substance mixture may be tested. The tubular element may have a housing section which may be at least partially transparent to the radiation for this purpose. The absorption according to the present invention may be adapted using an appropriate arrangement of the radiation unit and/or the tubular element.

An indirect measuring method may allow a relatively rapid testing to be implemented, requiring a comparatively small effort, for the development of materials and/or catalysts for the chemical conversion of a substance mixture. Using this method, the materials may, among other things, be divided into classes, e.g., into one class, which may include the materials that produce the desired substance, and into a second class, which may include the materials that do not produce the desired substance.

In general, there may be a close relationship between the intensity of absorption, and therefore the intensity of heating or non-heating of the reference substance and/or the chamber, and the quantity of the substance to be produced contained in the substance mixture. In this manner, besides detecting the desired product, the quantity of the substance to be produced may additionally be determined. For this purpose, an electrical analyzing unit having an appropriate stored characteristic map may be provided.

In principle, the substance mixture to be supplied to the device may include one single substance or multiple different substances, particularly gases.

DETAILED DESCRIPTION

Figure 1:
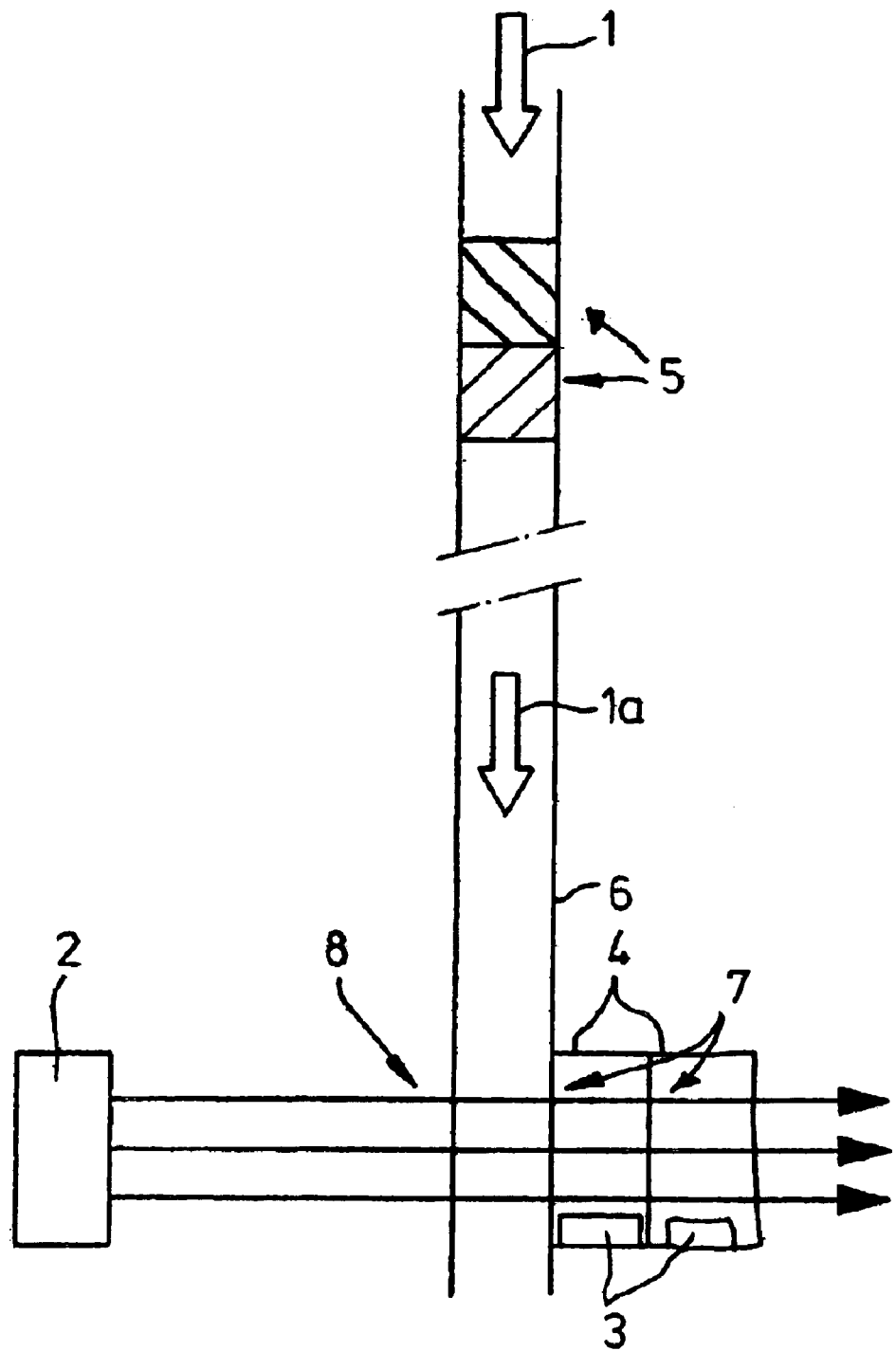
FIG. 1 shows an exemplary embodiment of the present invention.

FIG. 1 schematically shows an arrangement of components of an exemplary device according to the present invention. A gas mixture 1 flows through a tube 6. A material sample 5 is positioned inside tube 6. A measuring region 8 is provided behind material sample 5 in the flow direction, with, among other things, a chamber 4 filled with a reference gas 7 being positioned on tube 6. Both chamber 4 and tube 6 are configured to be transparent in the region of chamber 4 to infrared radiation from an infrared source 2.

Material sample 5 converts gas mixture 1 into a product mixture 1a, so that product mixture 1a may include a substance to be produced or a desired substance. Product mixture 1a absorbs at least a part of the radiation from IR source 2.

Alternatively, using a needle element, product mixture 1a may also be drawn off from a reactor, which may include material sample 5, and supplied to measuring region 8.

If product mixture 1a does not contain any substance to be produced or desired substance, which corresponds to reference gas 7, the radiation of IR source 2 penetrates tube 6, so that reference gas 7 absorbs the corresponding part of the radiation of IR source 2 and is thus heated. This heating of reference gas 7 is detected using a thermocouple 3 of chamber 4 and is communicated to an analyzing unit (not shown in detail) and appropriately analyzed.

If product mixture 1a contains the gas to be produced, which corresponds to reference gas 7, the radiation which reaches chamber 4 is appropriately reduced by the infrared absorption of the desired gas. Because of this, chamber 4 and/or reference gas 7 cools down, i.e., chamber 4 and/or reference gas 7 are not heated. The cooling or non-heating is also detected using thermocouple 3 and again communicated to and analyzed by the analyzing unit.

A testing unit, which may include numerous materials as shown in FIG. 1, may be provided for the development of materials 5 and/or catalysts 5. In this case, the container 1 holds a plurality of different materials 5 and substance mixture 1 is arranged to be chemically converted by at least one of the plurality of different materials 5. A radiation unit 2 is configured to generate a radiation that is at least partially absorbed by the converted substance mixture 1a. Chambers 4 are provided, each holding a reference substance 7 for a corresponding material to the tested. Temperature measuring devices 3 (e.g., thermocouple) are provided for each reference substance to measure a change in temperature in a corresponding reference substance caused by the absorption of radiation by the converted substance mixture 1a. In this regard, one thermocouple 3 and one chamber 4 may be provided for each material sample 5.

With the aid of appropriate testing units, numerous material samples 5 of greatly differing types may be characterized very rapidly in regard to their catalytic properties without great effort, which result in significant improvement, particularly, for example, in the development of catalysts.

What is claimed is:

1. A system for testing a material which includes a catalytically active material, comprising:

a container for holding the material and a substance mixture arranged to be chemically converted by the material to be tested;

a radiation unit configured to generate a radiation which is at least partially absorbed by the converted substance mixture;

a chamber for holding a reference substance and being reachable by the radiation that transmits through the converted substance mixture; and a temperature measuring device to measure a temperature change in the reference substance caused by the at least partial absorption of radiation by the converted substance mixture, wherein the reference substance has the same composition as the converted substance mixture.

2. The system according to claim 1, wherein the temperature measuring device is configured as a thermocouple.

3. The system according to claim 1, wherein the temperature measuring device is enclosed by the chamber.

4. The system according to claim 1, wherein the chamber includes a temperature regulation unit to regulate a chamber temperature.

5. The system according to claim 1, wherein the material to be tested is a powder.

6. The system according to claim 1, wherein the chamber includes a wall section which is at least partially transparent to the radiation.

7. The system according to claim 6, wherein the substance mixture is arranged between the chamber and the radiation unit.

8. The system according to claim 1, wherein:
the container comprises a tubular element portion within which to arrange the material to be tested.

9. The system according to claim 8, wherein the tubular element includes a housing section which is at least partially transparent to the radiation.

10. A method of testing a material which includes a catalytically active material, comprising:
chemically converting a substance mixture using the material being tested;
generating a radiation using a radiation unit;
directing the radiation at the converted substance mixture such that the radiation is at least partially absorbed by the converted substance mixture;
providing a reference substance at a location that is reachable by the radiation that transmits through the converted substance mixture; and
using the reference substance to indirectly measure a temperature change in the converted substance mixture caused by the absorption of radiation.

11. The method of claim 10, wherein the radiation unit generates an infrared radiation.

12. The method according to claim 10,
wherein the temperature is indirectly measured by directly measuring a temperature change in the reference substance caused by the radiation received by the reference substance.

13. A system for testing a material which includes a catalytically active material, comprising:
a container for holding the material and a substance mixture that is arranged to be chemically converted by the material to be tested by flowing though the container;
a radiation unit configured to generate a radiation which is at least partially absorbed by the converted substance mixture;
a chamber for holding a reference substance and being reachable by the radiation that transmits through the converted substance mixture; and
a temperature measuring device to measure a temperature change in the reference substance caused by the at least partial absorption of radiation by the converted substance mixture,
wherein the container comprises a tubular element portion within which to arrange the material to be tested, and
wherein the radiation unit is arranged to enable the radiation to penetrate the tubular element portion at a position downstream with respect to the material to be tested in a flow direction of the substance mixture.

14. A testing unit for testing a plurality of different materials, including catalytically active materials, comprising:
a container for holding the plurality of different materials and a substance mixture arranged to be chemically converted by at least one of the plurality of different materials;
a radiation unit configured to generate a radiation which is at least partially absorbed by the converted substance mixture;
a chamber for holding a reference substance for each corresponding different material, the chamber being reachable by the radiation that transmits through the converted substance mixture; and
a temperature measuring device for each different material to measure a temperature change in the corresponding reference substance caused by the at least partial absorption of radiation by the converted substance mixture.

15. The testing unit of claim 14, wherein the radiation unit is an infrared radiation unit.

* * * * *